United States Patent [19]

Kadowaki et al.

[11] Patent Number: 4,873,368

[45] Date of Patent: Oct. 10, 1989

[54] PROCESS FOR PRODUCING ACRYLIC ACID

[75] Inventors: Koju Kadowaki; Kohei Sarumaru, both of Ami; Takeshi Shibano, Yokkaichi, all of Japan

[73] Assignee: Mitsubishi Petrochemical Company Limited, Tokyo, Japan

[21] Appl. No.: 426,273

[22] Filed: Sep. 29, 1982

Related U.S. Application Data

[63] Continuation of Ser. No. 203,592, Nov. 3, 1980, abandoned.

[30] Foreign Application Priority Data

Nov. 19, 1979 [JP] Japan ................................. 54-149871

[51] Int. Cl.$^4$ ........................ C07C 51/25; C07C 57/05
[52] U.S. Cl. ..................................... 562/532; 562/534; 568/479
[58] Field of Search .................. 562/532, 534; 568/479

[56] References Cited

U.S. PATENT DOCUMENTS 3,717,675  2/1973  Sennewald et al. ................. 562/532
3,801,634  4/1974  Krabetz et al. ..................... 562/532
3,876,693  4/1975  Erpenbach et al. ................. 562/532
3,956,376  5/1976  Ferlazzo et al. .................... 562/532
4,031,135  6/1977  Engelbach et al. ................. 562/532
4,147,885  4/1979  Shimizu et al. ..................... 562/535

FOREIGN PATENT DOCUMENTS 939713  10/1963  United Kingdom .

Primary Examiner—Werren B. Lone
Assistant Examiner—Vera C. Clarke
Attorney, Agent, or Firm—Emmanuel J. Lobato; Robert E. Burns

[57] ABSTRACT

Propylene in admixture with molecular oxygen and steam is subjected to a two-step, vapor-phase, catalytic oxidation to convert into acrolein and then into acrylic acid. At least the first-step reaction is conducted in tubes of an apparatus of a shell-and-tube heat-exchanger type structure, and the reaction product of the first-step reaction is quenched before it is subjected to the second-step reaction. Reaction conditions in both the steps are specified.

7 Claims, 1 Drawing Sheet

PROCESS FOR PRODUCING ACRYLIC ACID

This is a continuation of application Ser. No. 203,592 filed 11-3-80, now abandoned.

BACKGROUND OF THE INVENTION

1. Field of the art

This invention relates generally to the production of acrylic acid, particularly to that by two-stage, vapor-phase, catalytic oxidation of propylene. More specifically, the invention relates to a process for producing acrylic acid by oxidizing propylene in a high concentration.

As a process for producing acrylic acid, the process of catalytically oxidizing propylene in two stages in the gas phase by using air is known and has already been reduced to industrial practice. In the first stage of this process, propylene is mixed and supplied with air and steam or an inactive gas such as nitrogen thereby to convert the propylene principally into acrolein and into acrylic acid in a by-procuct quantity. This first-stage outlet gas thus formed is fed as it is without separation of the products formed to the reaction vessel of the second stage.

Modification of this two-step method is also known where oxygen required for causing reaction in the second stage or steam is added anew to the above mentioned outlet gas.

In the second stage, the acrolein is converted principally into acrylic acid. The acrylic acid thus formed is generally cooled and, is separated as an aqueous solution thereof, and recovered from the gas flow, being passed through processes such as extractive distillation in the succeeding purification process step, thereby being isolated. The alternative method of precooling the second-stage outlet gas flow and then absorbing the acrylic acid with a suitable solvent thereby to separate the acrylic acid has also been proposed.

In this catalytic oxidation, the steam, which is one component of the feed gas, is necessary for the catalysis in the second stage wherein the acrolein is oxidized into acrylic acid. In addition, the steam serves also as a diluent for reducing the danger of explosion due to the mixing of the propylene or acrolein with oxygen to form an explosive gas mixture. However, if steam is used as a diluent in a great quantity, the aqueous solution of acrylic acid obtained in the recovery of acrylic acid by the ordinary cooling condensation method will be dilute, which will give rise to disadvantages such as an increase in the cost of separating the acrylic acid from the solution or an increase in the recovery loss of acrylic acid. Furthermore since the steam, itself entails a high cost, the use thereof in a great quantity, in any case, is uneconomical.

2. Prior art

For this reason, a method wherein, as a diluent for preventing the formation of an explosive composition within the range of inflammable mixture, a portion of the waste gas remaining after recovery and separation of acrylic acid and water, etc., from the outlet gas of the second-stage reactor by cooling, recovery with a solvent, or some other method, is recycled and substituted for steam has been proposed. The waste gas thus recycled comprises principally nitrogen, carbon dioxide, carbon monoxide, etc., but, depending on the reaction conditions, contains also unreacted propylene, acrolein, oxygen, and other gases. For example, Japanese Pat. Publn. No. 30688/ 1978, Pat. Laid Open Publn. No. 108917/1977, and Pat. Laid Open Publn. No. 15314/1978 disclose methods wherein the reaction waste gas is recycled to the first-stage inlet. Japanese Pat. Laid Open Publn. No. 36415/1976 discloses a method wherein the waste gas is divided and recycled to the first stage and the second stage.

In these processes, on the one hand, since the performances of their oxidation catalysts greatly influence their economies, a large number of proposals concerning catalysts for each stage have been made.

For example, catalysts for the oxidation of propylene into acrolein in the first stage are disclosed in Japanese Pat. Publn. Nos. 17711/1972, 27490/1972, 41329/1972, 42241/1972, 42813/1972, 1645/1973, 4763/1973, 4764/1973, 4765/1973, and others. Catalysts for the oxidation of acrolein into acrylic acid in the second stage are disclosed in Japanese Pat. Publn. Nos. 12129/1969, 19296/ 1973, 169/1974, 11371/1974, 10432/1977, and 31326/1977, and Japanese Pat. Laid-Open Publn. Nos. 2011/1971, 8360/ 1972, 43922/1974, 6117/1974, 124016/1974, 133317/1974, 25520/1975, 93918/1975, 23589/1977, 29483/1977, 29484/ 1977, and others.

Most of these catalysts are indicated as affording one-pass yields of the desired product of the order of 90 percent or higher, and it may be considered that, for the time being, sufficiently high yields of the desired product for economical carrying out of the processes of each stage are being obtained.

However, with respect to the object of economically producing acrylic acid, the prior and present technology cannot be said to be fully satisfactory. One important factor affecting this state of the art relates to the compositions of the feed materials. More specifically, first, an equimolar quantity of oxygen should be sufficient, theoretically, for oxidizing propylene to form acrolein in the first stage, and, if there are no other restrictions, the use of a volume of air which is 4.76 times relative to that of propylene, for example, will be sufficient. The propylene concentration in the gas mixture is thus 17.4 percent. In actual practice, however, a range of the propylene concentration of 4 to 7 percent is used in most cases. Accordingly, it can be said surplus gas which is excessive by the difference is being fed into the reactor.

As the materials to be fed into the second stage, oxygen required for the conversion of the acrolein formed in the first stage into acrylic acid (the theoretical oxygen quantity being $\frac{1}{2}$ mol of the acrolein) and steam in a quantity of the order of the same mol or more in view of the catalysis are necessary. Therefore, in the case where the feed gas to the first stage has a composition near the lower limits, replenishing of the oxygen and steam is necessary in an intermediate stage. However, various difficulties must be overcome in order to bring an industrial process close to such an ideal, and corresponding technical measures are necessary. One such measure is to cause the selectivity of the catalyst to approach 100 percent of the desired product. A second is a safety measure in the process.

The process of feeding starting gas of a high propylene concentration into the first stage and, at the outlet thereof, replenishing oxygen and steam and feeding the resulting mixture into the second stage thereby to produce acrylic acid is known through Japanese Pat. Laid Open Publn. No. 25521/1975. According to this publication, the desired product was obtained with a high spacetime yield by using a specific feed composition and a specific catalyst. However, according to our knowledge, there appears to be an unreasonable feature in this process in the removal of heat, and, moreover, there is no safety measure whatsoever, whereby it is not possible to apply this process to an industrial apparatus.

The measures which must be taken with regard to safety in the process are the avoidance of forming an explosive composition of propylene, acrolein, etc., and the prevention or suppression of a runaway or uncontrollable combustion reaction due to spontaneous oxidation of the acrolein at the outlet of the first stage. As a measure for avoiding the formation of an explosive composition, the admixing of an inactive gas such as steam, nitrogen, and carbon dioxide gas with the explosive gases thereby to form a gas outside of the explosion range (or range of inflammability) is generally resorted to. Since this explosion range varies with factors such as temperature, pressure, and the diluting gas, the selection of the conditions is important.

With respect to the combustion of acrolein at the first-stage outlet, the following countermeasures, for example, have been proposed. Japanese Pat. Laid Open Publn. No. 132007/1974 discloses a method wherein the reaction product gases are introduced from the outlet of the reaction zone directly into a directly adjoining heat-exchange zone and are cooled to a temperature of 200° to 300° C. by using water. Japanese Pat. Laid Open Publn. No. 36415/1976 discloses a method wherein air and waste gas are added to and mixed with a reaction gas mixture immediately after it has been discharged from the catalyst zone at a point to the rear of the first stage under rapid cooling to a mixing temperature of 150° to 320° C. Japanese Pat. Laid Open Publn. No. 15314/1978 discloses a method of restricting the oxygen concentration and adjusting it to a range of 1.2 to 1.6 times in terms of mols the propylene concentration.

In the method of Japanese Pat. Laid Open Publn. No. 132007/1974, however, there arises a problem in that the acrolein undergoes combustion before ample cooling can take place within the tubes of the heat-exchange zone. In the method of Japanese Pat. Laid Open Publn. No. 36415/ 1976, air and waste gas are added to the reaction gas mixture, but before these gases are thoroughly mixed and cooled, combustion of the acrolein similarly occurs. In the method of Japanese Pat. Laid Open Publn. No. 15314/ 1978, residual oxygen always exists because oxygen in excess of the oxygen required for the oxidation of the propylene is used, and under this condition it is virtually impossible to suppress the combustion of the acrolein. The methods of the above cited references are accompanied by these and other problems.

Thus, while these proposed methods have some meritorious effectiveness, it is difficult to say that these methods are fully satisfactory, and their practical application to industrial apparatus have still been inadequate.

SUMMARY OF THE INVENTION

With the aim of developing an industrially safe and economical process for producing acrylic acid by catalytic oxidation of propylene, we have carried out a study of the basic facts relating to such oxidation processes including a clarification of the characteristics of oxidation catalysts, precise measurement of the explosion range, and measurement of the rate of spontaneous oxidation of acrolein. As a result, we have been rewarded with the discovery of some new facts.

This invention has been developed on the basis of these new facts and, in its broadest aspect, provides a process which comprises carrying out high-concentration oxidation of propylene under specific and restricted conditions.

According to this invention, briefly summarized, there is provided a process for producing acrylic acid by a two-stage vapor-phase catalytic oxidation comprising subjecting a gas mixture containing propylene, molecular oxygen, and steam to a first-stage catalytic oxidation reaction thereby to convert propylene principally into acrolein and subjecting the gases formed in the first-stage catalytic oxidation reaction to a second-stage catalytic oxidation reaction thereby to convert the acrolein principally into acrylic acid, characterized in that it is carried out under the conditions:

A. that at least the first-stage catalytic oxidation reaction is carried out in a reaction zone defined by the conditions
  (1) that said reaction zone comprises a plurality of elongated unit reaction zones extending in the direction of flow of the gases and connected in parallel arrangement,
  (2) that each of the unit reaction zones comprises a reaction region comprising a bed of an oxidation catalyst and a cooling region comprising a bed of a solid inactive material disposed contiguously to the reaction region on the downstream side thereof, and
  (3) that the temperatures of the reaction region and of the cooling region are respectively controlled independently;

B. that the gases to be subjected to the first-stage catalytic oxidation reaction satisfy the conditions that the mol ratio of the molecular oxygen/the propylene is 1.17 to 1.66,
  that the mol ratio of the steam/the propylene is equal to or less than 4,
  that the propylene concentration is 7 to 15 percent, and
  that the gas pressure is 0.4 to 1.5 kg/cm$^2$ gage;

C. that the gases formed in the reaction regions of the unit reaction zones by the first-stage catalytic oxidation is quenched to a temperature of 280° C. or lower in the cooling region; and D. that the gases formed in the first-stage catalytic oxidation to be subjected to the second-stage catalytic oxidation reaction is conditioned by adding a gas mixture of molecular oxygen and steam to satisfy the conditions
  that the mol ratio of molecular oxygen/propylene is 1.75 to 2.5,
  that the mol ratio of steam/propylene is 1 to 5, and
  that the gas temperature is 280° C. or lower,
  the mol ratios being based on respective total quantities including those of the gases subjected to the first-stage catalytic oxidation reaction.

By the practice of the process of this invention, the propylene concentration, which has been of the order of 4 to 7 percent in prior-art processes, can be elevated to 7 to 15 percent, whereby an increase in the space-time yield can be realized. Since the propylene concentration is high, and the quantity of gas flowing through the reaction apparatus is small, the pressure loss is small, and, at the same time, a low-pressure reaction is possible. Futhermore, reaction conditions wherein the space velocity is low can be used without the accompaniment of a lowering of the space-time yield.

While these advantageous features contribute directly to reduction of utility costs, the possibility of low-pressure reaction affords a reduction of the resistance to diffusion within the catalyst particles and an improvement of selectivity. Furthermore, that the space velocity can be made low means that the one-pass yield of the desired product can be increased, and, in addition, that the reaction temperature can be lowered, whereby the cooling of the reactor outlet is facilitated.

Still another advantageous feature of the process of this invention is that the quantity of the steam used is small, the requirement for steam particularly in the first-stage reaction being so small that steam is almost unnecessary. Accordingly, without generating steam separately, the required steam can be obtained and supplied by causing the feed air to contact suitably warm water to cause a quantity thereof corresponding to the vapor pressure thereof to accompany the air. A corollary benefit arising from the small quantity of steam used is a high concentration of the aqueous solution of acrylic acid formed, as a result of which the cost of separating the acrylic acid is lowered.

In the case of two-stage oxidation of propylene, suppression of spontaneous oxidation of acrolein after the first-stage reaction is important, but the details of the nature of this spontaneous oxidation of acrolein have heretofore been unclear. As a result of our discovering that this reaction has a very great dependence on temperature, we have devised a specially designed first-stage reaction apparatus in accordance with this invention. By the use of this apparatus, as described hereinafter, rapid cooling is effectively achieved, and, as a result of this feature together with other necessary conditions, the danger of runaway combustion reaction due to spontaneous oxidation of acrolein is completely eliminated.

The nature, utility, and further features of this invention will be more clearly apparent from the following detailed description beginning with a consideration of basic and general aspects of the invention and concluding with a number of specific examples of practice thereof and comparison examples.

DETAILED DESCRIPTION OF THE INVENTION

1. First-Stage reaction apparatus 1.1. Shell-and-tube heat-exchanger type structure The process of this invention has a unique feature in the reaction zone for carrying out the first-stage reaction. This unique feature resides in the apparatus used as described hereinbelow.

This apparatus used in the first-stage reaction is, first of all, of the so-called shell-and-tube heat-exchanger type. A shell-and-tube heat-exchanger type reactor, itself, is known. In accordance with this invention, a bed of an oxidation catalyst is accommodated within each of a plurality of tubes corresponding to the cooling tubes of a shell-and-tube heat exchanger and thereby forms an elongated unit reaction zone. Through each of these unit reaction zones, the gas to be oxidized is caused to flow as a so-called tube fluid. On another hand, a suitable heating medium such as, for example, a liquid heating medium, is caused to flow as a so-called shell fluid in the spaces on the outer side of these tubes arranged parallelly in a bundle thereby to maintain the reaction temperature. The heating medium is ordinarily recirculated through an outside heat exchanger.

The plurality of these catalyst-filled tubes in parallel arrangement constitute the reaction zone of the first-stage catalytic oxidation reaction.

1.2. Reaction region

The above described catalyst bed within the catalyst-filled tubes constitutes the reaction region.

This invention is not characterized by the particular oxidation catalyst used therein, wherefor any catalyst which is capable of vapor-phase oxidizing propylene into acrolein in a high yield can be used. Specific examples of such a catalyst are disclosed in the publications referred to hereinbefore.

A catalyst which is particularly suitable for use in this invention is one which makes possible the production of a one-pass yield of approximately 88 percent or more, preferably approximately 90 percent or more for the sum of the quantities of the acrolein and acrylic acid at a reaction temperature of 280° to 350° C. A catalyst of this character can be selected from multiple-component catalysts containing Mo and Bi. One example of such a catalyst is as follows (reference being made to the specification of Japanese Pat. Appln. No. 8766/1979.)

$Mo_aBi_bNi_cCo_dFe_eNa_fMn_gB_hK_iSi_jO_x$

Here, the subscripts a through x represent atomic proportions of respective elements, and when a is 12, the values of the remaining subscripts are as follows.

| | |
|---|---|
| b = 4 to 7, | c = 0.05 to 5, |
| d = 0.05 to 5, | e = 0.05 to 2, |
| f = 0 to 1, | g = 0 to 1, |
| f + g = 0.01 to 1, | h = 0.02 to 2, |
| i = 0 to 1, | j = 6 to 48 | x is a number satisfying the valence of an element other than oxygen.

Depending on the necessity, the catalyst bed may be diluted with a filler comprising a solid inactive material such as that used in the cooling region, described hereinafter. Furthermore, a bed of a similar solid inactive material can be provided on the upstream side of the catalyst bed thereby to form a gas preheating region, as described in detail hereinafter. In addition, the catalyst bed may be so adapted that its catalytic activity varies in the direction of gas flowing therethrough.

In fact, a distribution of catalytic activity wherein the activity is low per unit volume from the inlet of the catalyst bed, where the heat generation is made intense in order to obtain a high space-time yield, to the middle part is effective for increasing the selectivity of the reaction and for prolonging the serviceable life of the catalyst. Such a distribution of catalytic activity is obtained by composing the catalyst bed with a number of catalysts in which their activities are successively increased from the inlet region to the outlet region, or by blending a diluent as mentioned hereinabove with a varied content thereof.

The particle size of the catalyst particles should be so determined in relation with the inner diameter of the reaction tubes used as to produce a suitable gas resistance and impart a suitable catalytic contact area. In general, the particle size is of the order of 2 to 8 mm.

1.3. Cooling region

The most unique feature of this invention relating to the reaction zone is the provision, as a cooling region, of a bed of a solid inactive material contiguous to and on the downstream side of the reaction region as described above in the unit reaction zones or the interiors of the reaction tubes. This cooling region formed by the bed of the solid inactive material is provided with means for controlling its temperature independently of the reaction region so that it can immediately and rapidly cool the gas formed by the first-stage reaction and flowing out from the reaction region, as described in detail hereinafter.

For the solid inactive material to be used in constituting the cooling region, almost any material which substantially does not have reaction activity with respect to the vapor-phase propylene, acrolein, and acrylic acid at a temperature in the vicinity of the catalytic oxidation reaction temperature can be used. Specific examples of such materials are α-alumina, alundum, mullite, carborundum, stainless steel, copper, aluminum, and ceramics. This material should be in a form in which its outer surface area is large such as, for example, small spheres, rings, small pieces, filament, meshes, and ribbons.

The bed of the solid inactive material of this character is contiguous to the bed of the oxidation catalyst. The term "contiguous to" as herein used means that the two beds are substantially contacting each other and should be interpreted to be of a degree of "substantially contacting each other" as viewed from the viewpoint of rapidly cooling the gas formed in the first-stage reaction.

The most typical mode in which the two beds are contiguous to each other is that wherein the catalyst bed and the bed of the solid inactive material are in direct contact with each other without anything interposed therebetween. In such a case, particles of the catalyst and the particulate solid inactive material are ordinarily intermixed at the interface or boundary between the two beds, and it is also possible to intentionally cause the two kinds of particles to coexist over a certain region on each side of the boundary between the two beds.

Instead of a direct contact of this nature between the two beds, the two beds can also be placed in mutual contact with a porous or perforated partition wall such as a metal wire mesh or a grating interposed therebetween. In this case, also, the catalyst particles and the particulate solid inactive material will probably be intermixed at the perforated portions of the partition wall.

1.4. Temperature control

According to this invention, the cooling region as described above is provided contiguous to the reaction region, and, as the temperatures of the two regions are controlled independently, the gas formed by the first-stage reaction is rapidly cooled to a temperature below 280° C.

As a result of our experiments, it was found that the velocity of spontaneous oxidation of acrolein increases at an accelerated rate with increase in the space volume for accommodating the acrolein (although there are some differences due to factors such as the shape of the space), that the apparent activation energy is 35 to 60 Kcal./mol (146 to 251 KJ/mol) and has a dependency on from the first to the second order of the partial pressure of the acrolein, and, from this result, that rapid cooling is effective for suppressing spontaneous oxidation of acrolein, and it is important to make the free space of the gas small. These new findings we have made have been utilized in practical form in the feature of this invention wherein a bed of the solid inactive material is provided as a cooling region contiguous to the reaction region, and the temperatures of the two regions are controlled separately.

The degree of the quenching is, in terms first of temperature, such that the gas temperature at the outlet of the cooling region is 280° C. or lower, preferably 260° C. or lower. The retention time in the cooling region should be made as short as possible, and the tube length and the temperature of the outside heating medium are so selected that this retention time will be 3 seconds or less, preferably 2 seconds or less. The lower limit of the gas temperature after cooling is a temperature above the dew point, but since cooling beyond necessity is uneconomical, it is preferably approximately 200° C. or higher. In passing, the temperature of the gas formed in the first-stage reaction at the reaction region outlet is usually of the order of 290° to 360° C.

For independent control of the temperatures of the reaction region and the cooling region, any suitable method can be used. One specific example of method is that wherein a partition plate is installed on the outer side of the reaction tubes perpendicular thereto at a position in the vicinity of the boundary between the reaction region and the cooling region, and a heating (or cooling) medium is supplied separately and independently to each of the regions. In another example of method, the reaction and cooling regions respectively reside in separate apparatus structures having respective groups of parallel tubes with tube ends, and these structures are joined with flanges in a state wherein the tubes in one structure are respectively alined with and facing corresponding tubes in the other structure.

1.5. Specific apparatus

Figure 1:
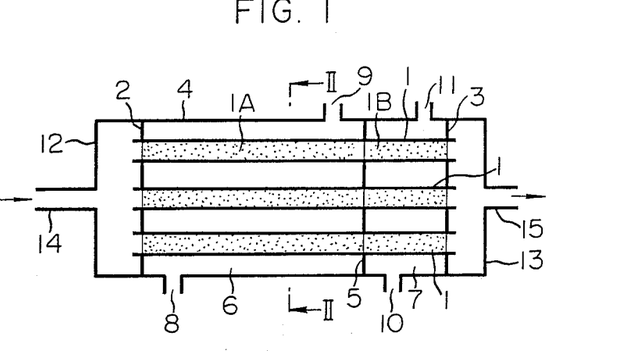
FIG. 1 is a schematic side view, in longitudinal section, showing one example of a first-stage reaction apparatus for practicing the process of this invention.
Figure 2:
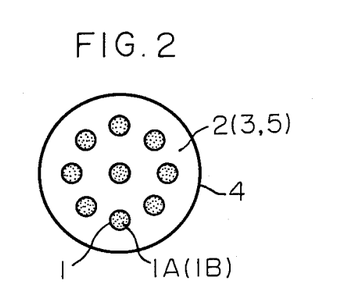
FIG. 2 is a cross section taken along the plane indicated by the line II—II in FIG. 1 as viewed in the arrow direction.

Referring to FIGS. 1 and 2, the example of a first-stage reaction apparatus illustrated schematically therein comprises, essentially, a plurality of reaction tubes 1 each providing a unit reaction zone, tube plates or sheets 2 and 3 for supporting the ends of the tubes 1 and forming therewith a bundle of tubes, and a cylinder or shell 4 in which the nest of tubes is housed. In each of the reaction tubes 1, a catalyst bed 1A and a bed of a solid inactive material 1B filled are accommodated respectively in the upstream and downstream portions thereof and respectively constitute a reaction region and a cooling region.

The space within the shell 4, outside of the tubes 1, is partitioned by a partition plate 5 disposed perpendicularly to the tubes 1 at a position corresponding to the boundary between the beds 1A and 1B. The interior space of the shell 4, outside of the tubes 1 and between the end sheets 2 and 3 is thereby divided into a chamber 6 surrounding the reaction region and a chamber 7 surrounding the cooling region. These chambers 6 and 7 are respectively provided with inlets 8 and 10 and outlets 9 and 11 for respective heating (or cooling) mediums. The inlet 8 and outlet 10 of the chamber 6 are so disposed that the heating medium for the reaction region will flow in the same direction as the gas flow through the tubes 1. This arrangement is effective in suppressing local generation of heat and smoothing the temperature distribution in the catalyst beds.

The two ends (upstream and downstream ends with respect to the gas flow) of the shell 4 extend axially upstream and downstream beyond the sheets 2 and 3, respectively, and are respectively closed by end plates 12 and 13, which are respectively provided with a gas inlet 14 and a gas outlet 15 communicating respectively with the header chambers or manifolds formed between the end plate 12 and the sheet 2 and between the end plate 13 and the sheet 3.

The feed gases for the first-stage reaction enter the apparatus through the inlet 14 and, as they pass through the tubes 1, undergo catalytic oxidation and rapid cooling, being sent out through the outlet 15. The gases formed in this manner by the first-stage reaction is replenished with molecular oxygen and steam and then sent to a second-stage reaction apparatus.

In an apparatus of this character, reaction tubes 1 each of an inner diameter of 15 to 40 mm, preferably 15 to 25 mm, are suitable, in general. A suitable tube length is, for example, of the order of 2,000 to 8,000 mm.

2. First-Stage reaction

2.1. Feed gases

Another unique feature of this invention is that the gases to be applied to the first-stage reaction is supplied under specific conditions as described below.

First, the concentration of the propylene in the feed gases is much higher than that ordinarily used, being from 7 to 15 percent.

A suitable value of the gas pressure at the inlet of the reactor is 0.4 to 1.5 kg/cm$^2$ gage, preferably 0.6 to 1.2 kg/cm$^2$ gage. An amply high productivity can be industrially attained within this range. We have found that at an inlet pressure higher than this range, heat removal is difficult, and a reaction of high conversion cannot be carried out. When the inlet pressure is lower than this range, the apparatus is uneconomical to use because of pressure loss.

The mol ratio of the molecular oxygen to the propylene should be between 1.17 and 1.66, preferably between 1.20 and 1.50. We have found that when this mol ratio is below 1.17, it is difficult to raise the propylene conversion even with the use of a high-selectivity catalyst. On the other hand, when this mol ratio exceeds 1.66, an excessive quantity of oxygen is used, which is counter to an object of this invention and, moreover, is not conducive to the prevention of explosion.

When this mol ratio of molecular oxygen to propylene is within the above state range, a reaction wherein the quantity in mols of the steam used is 4 times that of the propylene or less is possible. For achieving the objects of this invention, it is preferable that the quantity in mols of steam used be 2 times that of the propylene or less. Furthermore, a reaction in which steam is not used is also possible. The condition in this invention that the mol ratio of steam to the propylene be equal to or less than 4 is thus inclusive of the case where this mol ratio is zero.

Since a small quantity of steam used thus suffices, it is also possible to supply steam by causing the feed air to contact a suitable body of warm water and take up a quantity of steam corresponding to the vapor pressure into the air. For example, this may be accomplished by adjusting to a suitable temperature the waste water remaining after separation of acrylic acid by a step such as distillation or extraction from the aqueous solution of acrylic acid obtained by cooling the gas formed by the reaction and causing this waste water to undergo counterflow contact with the feed air thereby to cause water vapor to accompany the air. Another method which can be adopted comprises causing the gas obtained after separation of the greater part of condensable materials in the gas to undergo counterflow contact with water thereby to cause the water to absorb acrylic acid and/or acrolein remaining in the gas and causing this water to similarly contact the air.

It is also possible, in order to be outside of the explosion range, to use other inactive gases such as, for example, nitrogen, carbon dioxide, or the waste gas remaining after separation of materials such as the formed product from the second-stage outlet gases, as a substitute for steam or in addition to steam.

In the mixing step of the feed gases, the mixture passes through the explosion range. For this reason, it is preferable to adopt a mixer of a construction such that a gas mixture of homogeneous composition is obtained in a short time. It is recommended that the temperature at this time be 200° C. or lower, for greater safety 170° C. or lower. When, at a high temperature of approximately 300° C. or higher, this gas mixture is retained in an unpacked space, there is the danger of the propylene producing a cool frame and burning, although this differs depending on the composition and pressure. Accordingly, it is preferable, in the case where the gas mixture is to be preheated, to introduce it at a temperature of approximately 260° C. or lower into the reactor. Therefore, in the case where preheating of the feed gases up to the reaction temperature required by the catalyst is further necessary, the measure of providing as a preheating means a bed of particles of an inactive substance such as α-alumina, alundum, mullite, or carborundum at the inlets of the reaction tubes is recommended.

The gases for the first-stage reaction are essentially the same as the gases in the case where propylene is oxidized in vapor-phase into acrolein by a conventional process except for the above described characteristics. Accordingly, for the molecular oxygen, pure oxygen, air, or a mixture of pure oxygen or air with an inactive gas such as nitrogen or carbon dioxide is used.

2.2. Reaction

The first-stage reaction is ordinarily carried out under the conditions of a reaction temperature of 280° to 350° C. and a contact time of 2 to 10 seconds, although these conditions may differ with the catalyst used. For example, in the case where a multiple component catalyst based on Mo and Bi is used, it is used under the conditions of a reaction temperature of 290° to 340° C. and a contact time of the order of 3 to 8 seconds.

3. Second-Stage reaction

3.1. Second-Stage reaction apparatus

The second-stage reaction apparatus can be of any construction and structure suitable for and capable of receiving the gases formed in the first-stage reaction apparatus after air and steam have been added to these gases. Since the suppression of spontaneous oxidation of acrolein need not be considered in the second-stage reaction, quenching of the gases formed is not a requisite.

Accordingly, with respect to the catalyst bed, an apparatus of a fixed bed, moving bed, fluidized bed, or some other construction can be used. A specific example of a suitable apparatus is one using a fixed bed catalyst. From the viewpoint of facility in controlling the reaction temperature, an apparatus of shell-and-tube heat-exchanger type, as used in the first-stage reaction, is particularly suitable. As mentioned above, it is not necessary to provide a cooling region.

3.2. Feed gas for second-stage reaction

The feed gases for the second-stage reaction comprise the gases formed in the first-stage reaction and replenished molecular oxygen and steam necessary for the second-stage reaction.

The molecular oxygen and steam thus added should be homogeneously mixed with each other prior to being mixed with the formed gases of the first-stage reaction. The reason for this is that, although the temperature of the gases formed at the first-stage reaction is conditioned to be at 280° C. or lower in order to suppress the spontaneous oxidation (runaway combustion reaction), if air by itself is added to these gases, an explosive composition will be formed in the mixing step, which will be dangerous. This is also the reason why the composition of the feed gases for the second-stage reaction is limited within specific ranges. By observing these two precautions, the danger of explosion in the second-stage reaction can be completely eliminated.

In the composition of the feed gases for the second-stage reaction after the addition thereto of the molecular oxygen and steam, the quantity of the molecular oxygen in mols is 1.75 to 2.5 times that of propylene, while that of the steam is 1 to 5 times, both quantities being respective totals with the quantities supplied in the first-stage reaction. Preferable ranges of these quantities are respectively 1.8 to 2.1 times and 1.5 to 4 times. We have found that when the quantities of the molecular oxygen and the steam are both below their respective lower limits set forth above, the reaction velocity of the acrolein drops, and a high one-pass yield of acrylic acid may not be obtained. On the other hand, when the upper limits are exceeded, the quantity of the gases supplied into the second-stage reaction is large, which is counter to an object of this invention.

As a source of this molecular oxygen for replenishment, air is a simple and convenient source. As for the source of the steam, similarly as in the case of the feed steam for the first-stage reaction, the waste water obtained after separation of arylic acid from the aqueous solution of the acrylic acid formed or the water used in an auxiliary manner for obtaining a product formed such as acrylic acid from the gases formed can be caused to contact replenished air at a suitable temperature thereby to take up steam. Furthermore, provided that the above stated composition ranges are satisfied, other inactive gases such as, for example, a portion of the waste gases at the second-stage, can also be recycled and used.

The concentration of the steam in the replenishment gases, comprising a mixture of steam, air, and other inactive gases depending on the case, is dependent on factors such as the temperature and pressure at the time these gases are mixed into the flow of the gas formed at the first-stage reaction but a level of approximately 20 to 80 percent is usually used. More specifically, the procedure comprises setting the actual mixing conditions, determining the explosion range under these conditions, and determining a composition with a steam concentration which is greater than that required to be outside of the range and, at the same time, satisfies the compositional conditions for supply into the second stage.

3.3. Reaction

With regard to the second-stage reaction, also, this invention does not have an special feature in the oxidation catalyst used. Therefore, any catalyst which makes possible vapor-phase oxidation of acrolein with high yield into acrylic acid can be used. Specific examples of such catalysts are disclosed in the various publications cited hereinbefore.

Catalysts that are particularly suitable for use in this invention are those which exhibit performances such that the one-pass yield of acrylic acid from acrolein at a reaction temperature of 220° to 320° C. is approximately 90 percent or higher, preferably approximately 93 percent or higher. A catalyst of this character can be selected from among multiple-component catalysts each comprising Mo and V, one example having the following composition (reference being made to Japanese Pat. Laid Open Publn. No. 23589/ 1977).

$$Sb_aNi_bMo_cV_dW_eNb_fCu_gO_h$$

In this formula, the subscripts a through h respectively represent atomic ratios. When a is 100, b is 15 to 150, c is 10 to 500, d is 5 to 150, e is 0 to 100, f is 0 to 100, g is 0 to 50, g being not 0 when f is 0, and h is a number satisfying the valence of an element other than oxygen.

As to the kind, structural organization, and other particulars of the catalyst bed of the second-stage reaction, the considerations relating to the catalyst bed for the aforedescribed first-stage reaction can be applied provided that there is no adverse effect.

A reaction apparatus of shell-and-tube heat-exchanger type with reaction tubes of inner diameter of 15 to 40 mm, preferably 15 to 25 mm is suitable, similarly as in the case of the first-stage reaction apparatus.

The second-stage reaction is ordinarily carried out under the conditions of, for example, a temperature of 220° to 320° C. and a contact time of 1 to 10 seconds, although these conditions differ with the particular catalyst used. For example, in the case where a multiple-component catalyst based on Mo and V is used, the reaction in most cases is carried out with the condition ranges of the order of a reaction temperature of 230° to 290° C. and a contact time of 1 to 4 seconds.

3.4. Recovery of the acrylic acid

The separation of the acrylic acid from the gases formed in the second-stage reaction is carried out by an ordinary method. For example, after the gases formed have been cooled to 100° to 180° C. by means of heat exchanger they are caused to undergo counterflow contact with cold water containing a polymerization inhibitor or, depending on the case, cooled reaction liquor formed in the form of dew drops thereby to cause the gases to condense thereby to obtain an aqueous solution of acrylic acid. Then acrylic acid can then be isolated from this acrylic acid solution by a method such as extraction, distillation, or azeotropic distillation through the use of a suitable azeotropic agent of water.

4. Examples of experiments

Certain nomenclature and symbols used in the following examples of experiments are defined as follows. Catalyst composition: the composition of a compositeoxide catalyst is indicated by the atomic proportions of the constituent elements, except for oxygen. $C_3'$ designates propylene ACR designates acrolein AA designates acrylic acid Reaction temperature: average temperature of the heating medium in the reactor. Contact time (seconds) is equal to the apparent volume (liter) of the charged catalyst multiplied by 3,600 and divided by the volumetric flow rate (liter/hr) of the feed gas under reaction temperature and pressure.

EXAMPLES 1, 2, AND 3 AND COMPARISON EXAMPLES 1 AND 2

These experiments relate to only a study of the composition of the feed gas of the first-stage reaction.

As a catalyst for oxidation of propylene, the composite-oxide catalyst of the following composition was prepared by an ordinary method. The particle size was 5-mm diameter × 3 mm.

$$Mo_{12}Bi_5Ni_3Co_2Fe_{0.4}Na_{0.2}B_{0.2}K_{0.15}Si_{24}$$

The reactor was made of stainless steel and was of a double-tube construction wherein the inner tube was of 20-mm inner diameter and 2,200-mm length, and the outer tube was of 100-mm inner diameter and 1,900-mm length. The inner tube was packed with the catalyst. The space between the inner and outer tubes was filled with a nitrate bath as a heating medium, which was maintained at a constant temperature by agitation. In the reaction tube inlet end, mullite balls of 4-mm diameter were placed as a preheating means in a bed over 200 mm in the longitudinal direction. 250 ml of the above mentioned particulate catalyst was mixed with an equal quantity of mullite balls as a diluent and packed into the inner tube, and the reaction tube at its outlet portion was filled with mullite balls.

The feed gas was preheated to approximately 180° C., and air and steam were admixed therewith. Then propylene was admixed, and the resulting gas mixture was caused to flow through the reaction tube. At the reaction tube outlet, the gas mixture was cooled to approximately 10° C. by a tube-type cooler provided there and then passed through a gas-liquid separator, and the gas mixture was adjusted for its pressure and discharged. The results of the reaction when the feed gas composition was changed are indicated in Table 1. Even when the propylene concentration in the feed gas is high, the desired product was obtained in a high yield provided that the composition was within the limits specified by this invention.

TABLE 1

|  |  | Example 1 | Example 2 | Example 3 | Comparison Example 1 | Comparison Example 2 |
|---|---|---|---|---|---|---|
| Feed composition |  |  |  |  |  |  |
| $C_3'$ | % | 9 | 12 | 14 | 9 | 12 |
| Steam | " | 30 | 10 | 3 | 44 | 25 |
| Air | " | 61 | 78 | 83 | 47 | 63 |
| Steam/$C_3'$ | mol/mol | 3.3 | 0.83 | 0.21 | 4.9 | 2.1 |
| $O_2/C_3'$ | " | 1.43 | 1.37 | 1.25 | 1.09 | 1.11 |
| Reaction temperature | °C. | 310 | 310 | 320 | 320 | 320 |
| Reaction pressure | Kg/cm$^2$G | 1.0 | 1.0 | 1.0 | 1.0 | 1.0 |
| Contact time | second | 5.7 | 5.7 | 5.7 | 5.7 | 5.7 |
| $C_3'$ conversion | % | 98.8 | 98.5 | 97.3 | 87.0 | 89.6 |
| ACR yield | " | 79.5 | 80.2 | 81.1 | 70.0 | 72.3 |
| AA yield | " | 12.1 | 11.7 | 9.3 | 10.6 | 10.9 |
| ACR + AA yield | " | 91.6 | 91.9 | 90.4 | 80.6 | 83.2 |
| ACR + AA selectivity | " | 92.7 | 93.3 | 92.9 | 92.6 | 92.9 |

EXAMPLES 4 AND 5 AND COMPARISON EXAMPLES 3 AND 4

These examples relate to only a study of the feed gas composition of the second-stage reaction.

Two-stage continuous reaction was carried out by using two reactors each of the same type as that used in Example 1. For the first stage, the same reactor as used in Example 2 was used, and in the second stage, a catalyst of the following composition for oxidation of acrolein was prepared and used. The particle size of this catalyst was 5-mm diameter × 3 mm.

$$Sb_{100}Ni_{43}Mo_{35}V_7Nb_3Cu_3Si_{80}$$

167 ml of this catalyst was diluted with the same quantity of mullite balls, and the resulting mixture was charged into the second-stage reaction tube in the same manner as in the first-stage reaction tube.

A nozzle was provided in an intermediate part of each stage to afford injection of intermediate air. The piping at these parts was maintained at approximately 250° C. The feed gas was supplied into the first-stage reaction tube under the same conditions as in Example 2, and the oxidation reaction of the second stage was caused by injecting and admixing a gas mixture of air and steam through the intermediate nozzles. The outlet gases thus obtained were cooled to separate the gas and liquid phases, and the gas mixture was adjusted for its pressure and discharged. The reaction results obtained when the composition of gases supplied to the second-stage reaction was varied by changing the rate of injection through the intermediate nozzle are set forth in Table 2.

TABLE 2

|  |  | Exam. 4 | Exam. 5 | Comparsion Exam. 3 | Comparison Exam. 4 |
|---|---|---|---|---|---|
| 1st-Stage reaction |  |  |  |  |  |
| $C_3'$ conversion | % | 98.5 | same as at left | same as at left | same as at left |
| ACR yield | " | 80.2 | " | " | " |
| AA yield | " | 11.7 | " | " | " |
| 2nd-Stage feed* |  |  |  |  |  |
| Total flow rate | l/h | 257 | 240 | 200 | 240 |
| Composition |  |  |  |  |  |
| $C_3'$ | % | 7 | 7.5 | 9 | 7.5 |

TABLE 2-continued

|  |  | Comparsion | Comparison |
|---|---|---|---|
|  |  | Exam. 4 | Exam. 5 | Exam. 3 | Exam. 4 |

|  |  | Exam. 4 | Exam. 5 | Exam. 3 | Exam. 4 |
|---|---|---|---|---|---|
| steam | " | 26.5 | 15 | 7.5 | 35 |
| air | " | 66.5 | 77.5 | 83.5 | 57.5 |
| Steam/C3' | mol/mol | 3.8 | 2.0 | 0.83 | 4.7 |
| O2/C3' | " | 2.00 | 2.17 | 1.95 | 1.61 |
| Reaction temperature | °C. | 260 | 265 | 270 | 270 |
| Reaction pressure | Kg/cm²G | 1.0 | " | " | " |
| Contact time | second | 2.4 | 2.5 | 3.0 | 2.4 |
| Over-all reaction results |  |  |  |  |  |
| C3' conversion | % | 98.7 | 98.6 | 98.8 | 98.6 |
| ACR yield | " | 0.3 | 0.4 | 6.8 | 8.0 |
| AA yield | " | 87.8 | 87.8 | 81.4 | 79.9 |

*Total quantity supplied in first stage and intermediate part.

EXAMPLES 6 THROUGH 9 AND COMPARISON EXAMPLES 5, 6, AND 7

These examples relate to only a study of the suppression of spontaneous oxidation of acrolein. With the aim of determining the quantity of spontaneous oxidation of acrolein at the outlet of the first-stage reactor, the quantity of reaction within a stainless-steel tube coupled directly to the reaction tube was measured as the temperature of and packed material within the stainless-steel were varied. The reaction conditions of the first stage were held constant, and the composition of the formed gases was substantially as follows. In each of the individual experiments, the composition of the gases when they were rapidly cooled at the reaction tube outlet was measured each time, and, from the corresponding measurement of the composition of the gases at the stainless-steel tube outlet, the reaction quantity was calculated.

The composition of the gases formed in the first stage was as follows.

| acrolein | 5.95% |
|---|---|
| acrylic acid | 0.95% |
| propylene | 0.14% |
| oxygen | 4.80% |
| steam | 35.3% |
| nitrogen and others | 52.9% |

Outlet pressure: 1.0 kg/cm² gage. The relationship between conditions relating to the tubes and the reaction quantity is indicated in Table 3. In Table 3, the term "reaction quantity" represents the total yield decrease (percent) of the acrolein and the acrylic acid.

TABLE 3

|  | Inner diam. (mm) | Length (mm) | Temperature (°C.) | Retention time (sec.) | Packing (mm) | Reaction quantity (%) |
|---|---|---|---|---|---|---|
| Example 6 | 27 | 1900 | 280 | 6.5 | — | <0.2 |
| Example 7 | " | " | 320 | " | mullite balls (5 mm diam.) | <0.2 |
| Example 8 | " | " | 320 | " | stainless-steel Raschig rings (5 mm diam. × 2 mm diam. × 5 mm) | <0.2 |
| Example 9 | 21 | 830 | 320 | 1.8 | 10-mesh wire mesh* | <0.2 |
| Comparison Example 5 | 27 | 1900 | 300 | 6.5 | — | 1.1 |
| Comparison Example 6 | " | " | 320 | " | — | 4.6 |
| Comparison Example 7 | 21 | 830 | 320 | 1.8 | — | 1.1 |

(*)Wire diameter 0.2 mm, stainless steel, 55 grams.

From the results of Example 6 and Comparison Example 5, it is apparent that, if the space temperature is 280° C. or lower, the spontaneous oxidation quantity can be reduced to 0.2 percent or less even when the retention time is long. From the results of Examples 7 and 8 and Comparison Example 6, it is apparent that even if the temperature is 320° C., if a packing material such as mullite balls or stainless-steel Raschig rings are used, spontaneous oxidation can be remarkably suppressed and can be neglected. From the results of Example 9 and Comparison Example 7, it is seen that a wire mesh has a similar effectiveness. Furthermore, from the results of Comparison Example 7, it is apparent that, since there is a reaction loss of 1.1 percent at 320° C. even with a retention time of 1.8 seconds in a tube of an inner diameter of 21 mm, an empty tube is unsuitable for use as the cooling tube at the first-stage outlet.

EXAMPLE 10

This example relates to a two-stage continuous reaction.

This reaction was carried out in first-stage and second-stage reactors each comprising a shell-and-tube heat-exchanger type reactor having four reaction tubes of stainless steel each of 20-mm inner diameter and 3-meter length and using circulating nitrate bath as a heating medium on the shell side. A cooling region comprising four tubes of the same diameter as the reaction tubes and 800-mm length confronting and coaxially alined with respective reaction tubes was connected by means of a flange directly to the outlet of the first-stage reactor. The tubes of this cooling region were cooled on the shell side by the molten nitrate agitated by bubbling air. Immediately downstream from this cooling region, nozzles were provided to supply intermediate air. The gas from the outlet of the second-stage reactor was cooled by means of a tube-type heat exchanger, and an aqueous solution of acrylic acid was recovered with a gas-liquid separator.

In the first-stage reactor, a catalyst of the following composition prepared similarly as in Example 1 was packed in a quantity of 700 ml into each reaction tube, 200 ml of which on the inlet side was diluted with 100 ml of Raschig rings, and the outlet side of each reaction tube was packed with Raschig rings.

$Mo_{12}Bi_5Ni_3Co_2Fe_{0.4}Na_{0.2}B_{0.2}K_{0.15}Si_{24}$

Each cooling tube was uniformly packed with approximately 55 g of 10-mesh stainless-steel wire mesh.

In the second-stage reactor, a catalyst of the following composition for oxidation of acrolein was packed in a quantity of 500 ml into each reaction tube, 150 ml of which at the inlet part was diluted with 75 ml of Raschig rings similarly as in the first-stage reaction tubes.

$Sb_{100}Ni_{43}Mo_{35}V_7Nb_3Cu_3Si_{80}$

The above described apparatus was used to carry out the process of this invention by heating the first-stage reactor to 320° C., adjusting the temperature of the outlet cooler to 260° C., and heating the second-stage reactor to 265° C. For the feed gas, a gas mixture of 12 percent of propylene, 10 percent of steam, and 78 percent of air was supplied at a flow rate of 1,960 liters per hour (based on 0° C. and one atmosphere of pressure as standard conditions, which will apply hereinafter) into the first-stage reactor, and a gas mixture of 40 percent of steam and 60 percent of air was supplied through the intermediate nozzle at a flow rate of 1,120 liters per hour, the gases being caused to flow through the reaction systems as the pressure thereof was adjusted to 1.0 kg/cm² gage.

The results of the reactions were as set forth in Table 4. No variation with elapse of time was observable from the third day to the 60th day, and it was possible to carry out the process operation in a stable manner with respect to conditions such as temperatures at various parts. Furthermore, upon completion of the experiment, the cooling region parts, the intermediate nozzles, and other parts were disassembled and inspected, whereupon no abnormalities were found.

TABLE 4

| Days elapsed | $C_3'$ conversion (%) | ACR yield (%) | AA yield (%) | Concentration of acrylic acid in solution formed (% by weight) |
|---|---|---|---|---|
| 1 day | 98.8 | 0.1 | 86.5 | 46.1 |
| 3 days | 98.3 | 0.2 | 87.6 | 46.7 |
| 60 days | 98.1 | 0.2 | 87.8 | 46.9 |

What is claimed is:
1. In a process for producing acrylic acid by a two-stage gas-phase catalytic oxidation comprising subjecting a gas mixture containing propylene, molecular oxygen, and steam to a first-stage catalytic oxidation reaction thereby to convert propylene principally into acrolein and subjecting the gases formed in the first-stage catalytic oxidation reaction to a second-stage catalytic oxidation reaction thereby to convert the acrolein principally into acrylic acid, the improvement wherein said process is carried out under the conditions comprising:
A. carrying out at least the first-stage catalytic oxidation reaction in a reaction zone defined by the conditions
  (1) that said reaction zone comprises a plurality of elongated unit reaction zones extending in the direction of flow of the gases and connected in parallel arrangement,
  (2) that each of the unit reaction zone comprises a reaction region comprising a bed of oxidation catalyst capable of a one pass yield of at least about 88% for the sum of the quantities of acrolein and acrylic acid at a reaction temperature of about 280° to 350° C. and a cooling region comprising a bed of a solid inactive material disposed contiguously to the reaction on the downstream side thereof, and
  (3) that the temperatures of the reaction region and of the cooling region are respectively controlled independently;
B. that the gases to be subjected to the first-stage catalytic oxidation reaction satisfy the conditions:
  that the mol ratio of molecular oxygen/propylene is 1.17 to 1.66, that the mol ratio of steam/propylene is equal to or less than 4,
  that the propylene concentration is 7 to 15 percent, and
  that the gas pressure is 0.4 to 1.5 kg./cm.² gage;
C. that the gases formed in the reaction regions of the unit reaction zones by the first-stage catalytic oxidation are quenched to a temperature of 280° C. or lower in the cooling region; and
D. that the gases formed in the first-stage catalytic oxidation reaction to be subjected to the second-stage catalytic oxidation reaction are conditioned by adding a gas mixture of molecular oxygen and steam to satisfy the conditions:
  that the mol ratio of molecular oxygen/propylene is 1.75 to 2.5,
  that the mol ratio of steam/propylene is 1 to 5, and
  that the gas temperature is 280° C. or lower, the mol ratios being based on respective total quantities including those of the gases subjected to the first-stage catalytic oxidation reaction.
2. The process defined in claim 1 wherein said gas mixture subjected to said first-stage catalytic oxidation consist essentially of propylene, steam and a molecular oxygen-containing gas selected from at least one member of the group consisting of molecular oxygen, air and a mixture thereof with inactive gas.
3. The process defined in claim 1 wherein said second-stage catalytic oxidation is carried out by means of a catalyst capable of a one pass yield of acrylic acid from acrolein of at least about 90% at a reaction temperature of about 220° to 320° C.
4. The process defined in claim 1 in which said gases formed by said first-stage catalytic oxidation are quenched to a temperature of about 280° to 200° C. in a period of about 3 seconds or less.
5. The process defined in claim 1 in which the gases to be subjected to said first-stage catalytic oxidation satisfy the conditions:
  that the mol ratio of molecular oxygen/propylene is about 1.20 to 1.50,
  that the mol ratio of the steam/propylene is about equal to or less than 2,
  that the gas pressure is 0.6 to 1.2 kg./cm.² gage,
  that the reaction temperature in said first stage oxidation is about 280° to 350° C., and
  that the contact time is about 2 to 10 seconds; the gases formed by the first-stage catalytic oxidation are quenched to a temperature of about 260° to 200° C. within a period of about 2 seconds or less; and the conditions satisfied in said second-stage catalytic reaction are:
  a mol ratio of molecular oxygen/propylene of about 1.8 to 2.1,
  a mol ratio of steam/propylene of about 1.5 to 4 and a contact time of about 1 to 10 seconds.

6. The process defined in claim 2 in which said gases formed by said first-stage catalytic oxidation are quenched to a temperature of about 280° to 200° C. in a period of about 3 seconds or less.

7. The process defined in claim 2 in which the gases to be subjected to said first-stage catalytic oxidation satisfy the conditions:

that the mol ratio of molecular oxygen/propylene is about 1.20 to 1.50, that the mol ratio of the steam/propylene is about equal to or less than 2, that the gas pressure is 0.6 to 1.2 kg./cm.$^2$ gage, the reaction temperature in said first stage oxidation is about 280° to 350° C. and the contact time is about 2 to 10 seconds; the gases formed by the first-stage catalytic oxidation are quenched to a temperature of about 260° to 200° C. within a period of about 2 seconds or less; and the conditions satisfied in said second-stage catalytic reaction are:

a mol ratio of molecular oxygen/propylene of about 1.8 to 2.1, a mol ratio of steam/propylene of about 1.5 to 4 and a contact time of about 1 to 10 seconds.

* * * * *